(12) United States Patent
Stith et al.

(10) Patent No.: US 12,390,110 B2
(45) Date of Patent: *Aug. 19, 2025

(54) MEDICAL IMAGING SYSTEMS AND METHODS

(71) Applicant: Intuitive Surgical Operations, Inc., Sunnyvale, CA (US)

(72) Inventors: Curtis W. Stith, Santa Cruz, CA (US); Jeffrey M. DiCarlo, Austin, TX (US); Changmeng Liu, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/680,295

(22) Filed: May 31, 2024

(65) Prior Publication Data

US 2024/0315562 A1 Sep. 26, 2024

Related U.S. Application Data

(63) Continuation of application No. 17/294,195, filed as application No. PCT/US2019/063182 on Nov. 26, 2019, now Pat. No. 12,035,997.

(Continued)

(51) Int. Cl.
*A61B 5/00* (2006.01)
*A61B 1/00* (2006.01)
(Continued)

(52) U.S. Cl.
CPC ...... *A61B 5/0071* (2013.01); *A61B 1/000096* (2022.02); *A61B 1/043* (2013.01);
(Continued)

(58) Field of Classification Search
None
See application file for complete search history.

(56) References Cited

U.S. PATENT DOCUMENTS 12,035,997 B2 7/2024 Stith et al.
2001/0007921 A1 7/2001 Hayashi
(Continued)

FOREIGN PATENT DOCUMENTS

CN 204887163 U 12/2015
EP 2017591 A1 1/2009
(Continued)

OTHER PUBLICATIONS

International Search Report and Written Opinion for Application No. PCT/US2019/063182, mailed on Mar. 20, 2020, 11 pages.

(Continued)

*Primary Examiner* — John P Leubecker

(57) ABSTRACT

An illustrative system includes an image sensor comprising a first pixel, a second pixel, a third pixel, and a fourth pixel. The system further includes a pixel-level broadband infrared cutoff filter that covers the second pixel and that is configured to prevent the second pixel from collecting infrared light having wavelengths included in a first range of wavelengths. The first, third, and fourth pixels are not covered by pixel-level broadband infrared cutoff filters configured to prevent the first, third, and fourth pixels from collecting infrared light having wavelengths included in the first range of wavelengths.

14 Claims, 15 Drawing Sheets

Related U.S. Application Data

(60) Provisional application No. 62/774,041, filed on Nov. 30, 2018.

(51) Int. Cl.
*A61B 1/04* (2006.01)
*A61B 1/05* (2006.01)
*A61B 1/06* (2006.01)

(52) U.S. Cl.
CPC .............. *A61B 1/05* (2013.01); *A61B 1/0638* (2013.01); *A61B 1/0646* (2013.01)

(56) References Cited

U.S. PATENT DOCUMENTS

| | | | |
|---|---|---|---|
| 2003/0216626 A1* | 11/2003 | Tsujita | A61B 5/0084 600/321 |
| 2006/0241496 A1 | 10/2006 | Fengler et al. | |
| 2008/0239070 A1 | 10/2008 | Westwick et al. | |
| 2009/0021739 A1 | 1/2009 | Tsujita et al. | |
| 2011/0063427 A1 | 3/2011 | Fengler et al. | |
| 2011/0279716 A1 | 11/2011 | Shintani | |
| 2012/0056073 A1 | 3/2012 | Ahn | |
| 2012/0257030 A1* | 10/2012 | Lim | A61B 1/000094 348/70 |
| 2013/0041221 A1 | 2/2013 | McDowall et al. | |
| 2015/0221691 A1 | 8/2015 | Watanabe | |
| 2015/0381909 A1 | 12/2015 | Butte et al. | |
| 2016/0055821 A1* | 2/2016 | Phan | G09G 5/026 345/592 |
| 2017/0134650 A1* | 5/2017 | Seger | H04N 23/57 |
| 2017/0289467 A1* | 10/2017 | Yamamoto | H04N 23/11 |
| 2018/0184054 A1* | 6/2018 | Lundberg | G02B 5/208 |
| 2019/0206917 A1* | 7/2019 | Nakajiki | H10F 39/8053 |
| 2019/0378868 A1* | 12/2019 | Takahashi | H10F 39/18 |
| 2021/0137369 A1 | 5/2021 | Meester | |
| 2022/0007925 A1 | 1/2022 | Stith et al. | |

FOREIGN PATENT DOCUMENTS

| | | |
|---|---|---|
| JP | 2007089840 A | 4/2007 |
| JP | 2009066121 A | 4/2009 |
| JP | 2010022700 A | 2/2010 |
| JP | 2011200534 A | 10/2011 |
| JP | 2011528918 A | 12/2011 |
| JP | 2015112208 A | 6/2015 |
| JP | 2016058866 A | 4/2016 |
| JP | 2017225736 A | 12/2017 |
| KR | 101723794 B1 | 4/2017 |
| WO | WO-2009117483 A1 | 9/2009 |
| WO | WO-2016194101 A1 | 12/2016 |
| WO | WO-2018164579 A1 | 9/2018 |
| WO | WO-2018211885 A1 | 11/2018 |

OTHER PUBLICATIONS

International Preliminary Report on Patentability for Application No. PCT/US2019/063182, mailed on Jun. 10, 2021, 8 pages.

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

1

MEDICAL IMAGING SYSTEMS AND METHODS

RELATED APPLICATIONS

The present application is a continuation of U.S. patent application Ser. No. 17/294,195, filed May 14, 2021 and issued as U.S. Pat. No. 12,035,997, which is a U.S. National Stage Application under 35 U.S.C. § 371 of International Application No. PCT/US2019/063182, filed Nov. 26, 2019, which claims priority to U.S. Provisional Patent Application No. 62/774,041, filed Nov. 30, 2018, each of which is hereby incorporated by reference in its entirety.

BACKGROUND INFORMATION

A conventional image sensor included in an imaging device typically includes an array of pixels (also called photosites or photosensors) that each detect light that reflects from surfaces in a scene. The detected light may then be converted into data representative of an image of the scene.

To facilitate generation of a color image, an image sensor may include an arrangement of color filters that cover the pixels. Each color filter is configured to allow its corresponding pixel to detect only a particular color component of light incident on the pixels. For example, a conventional color filter arrangement (e.g., a Bayer filter arrangement) is fifty percent green, twenty-five percent red, and twenty-five percent blue. In other words, for every two-by-two pixel array included in an image sensor, two of the pixels are covered by a green filter configured to allow the two pixels to detect only a green component of visible light, one of the pixels is covered by a red filter configured to allow the pixel to detect only a red component of visible light, and one of the pixels is covered by a blue filter configured to allow the pixel to detect only a blue component of visible light. Such color filter arrangements are commonly referred to as RGGB, BGGR, RGBG or GRGB. Unfortunately, such color filter arrangements are not well suited for medical applications in which images of internal anatomy are acquired using an imaging device (e.g., an endoscope) configured to be positioned within a patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
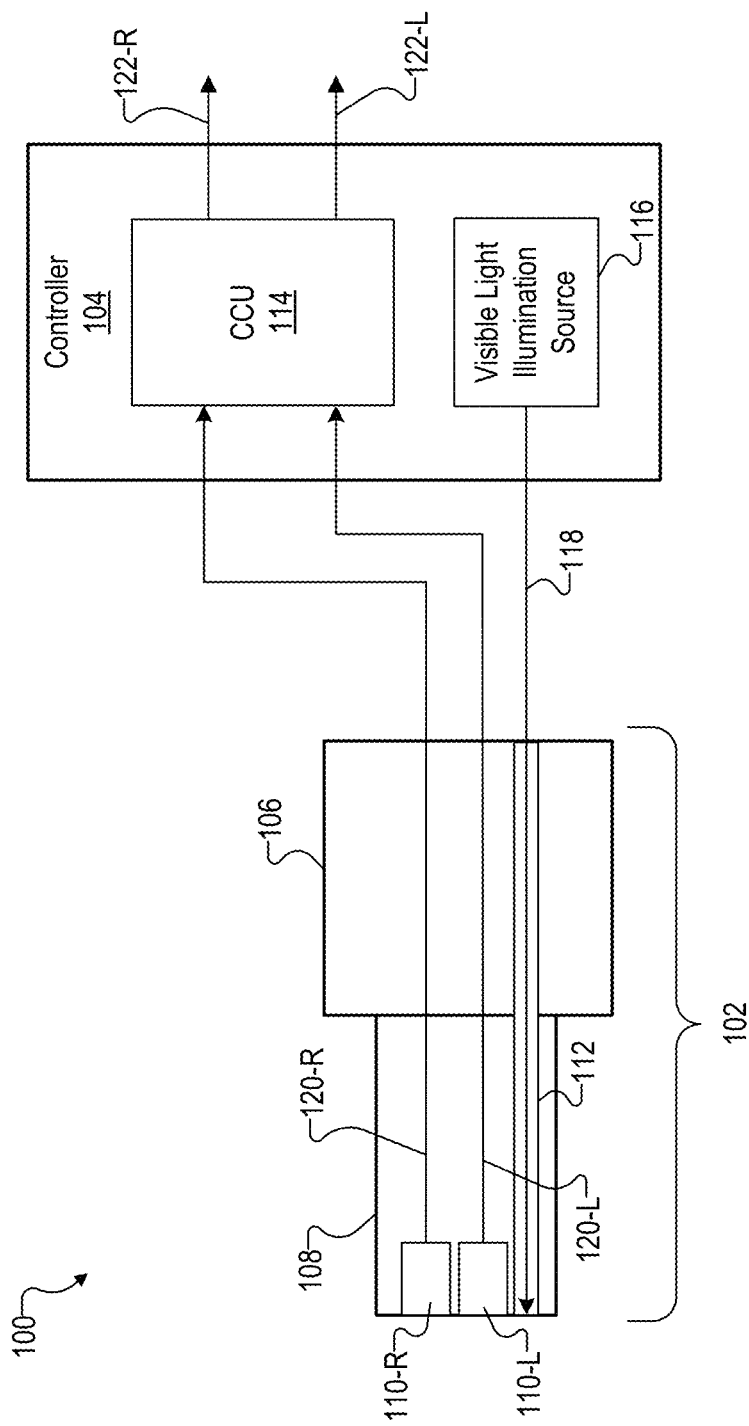
FIG. 1 illustrates an exemplary medical imaging system according to principles described herein.

Medical imaging systems and methods are described herein. As will be described in more detail below, an exemplary medical imaging system includes an image sensor comprising a two-by-two array of pixels. The two-by-two array includes a first pixel, a second pixel, a third pixel, and a fourth pixel. A red filter covers the first pixel, a first blue filter covers the second pixel, a second blue filter covers the third pixel, and a green filter covers the fourth pixel. The red filter is configured to allow the first pixel to collect a red component of visible light and prevent the first pixel from collecting blue and green components of the visible light. The first and second blue filters are configured to allow the second and third pixels to each collect the blue component of the visible light and prevent the second and third pixels from each collecting the red and green components of the visible light. The green filter is configured to allow the fourth pixel to collect the green component of the visible light and prevent the fourth pixel from collecting the red and blue components of the visible light.

Various advantages and benefits are associated with the medical imaging systems and methods described herein. For example, it is often desirable to use blue-biased illumination (i.e., light that has more of a blue component than green or red components) in medical imaging applications. This is because the wavelengths of the green and red components are longer than the blue component and therefore penetrate deeper into patient anatomy. This, in turn, causes the green and red components to scatter more than the blue component, resulting in the red and green components being relatively more blurry in images captured by an imaging device. Hence, in medical imaging applications, blue-biased illumination results in sharper images than illumination that is biased to other colors (e.g., green). By configuring fifty percent of the pixels in a two-by-two pixel array to capture the blue component of light, the systems and methods described herein may more effectively capture the blue-biased light and therefore produce sharper and more accurate images of the patient anatomy.

Another exemplary medical imaging system described herein includes an image sensor comprising a two-by-two array of pixels that includes a first pixel, a second pixel, a third pixel, and a fourth pixel. A first color filter covers the first pixel and is configured to allow the first pixel to collect a first color component of visible light and prevent the first pixel from collecting second and third components of the visible light. A second color filter covers the second and third pixels. The second color filter is configured to allow the second and third pixels to each collect the second color component of the visible light and prevent the second and third pixels from each collecting the first and third color components of the visible light. A third color filter covers the fourth pixel and is configured to allow the fourth pixel to collect the third color component of the visible light and prevent the fourth pixel from collecting the first and second color components of the visible light. A pixel-level broadband infrared cutoff filter covers the second pixel and is configured to prevent the second pixel from collecting infrared light having wavelengths included in a first range of wavelengths. In some examples, a narrowband infrared cutoff filter covers the first, third, and fourth pixels and is configured to prevent the first, third, and fourth pixels from collecting infrared light having a wavelength included in a second range of wavelengths. The second range of wavelengths is included in and narrower than the first range of wavelengths. As will be described below, this configuration advantageously provides three color component channels and a fluorescence illumination channel that may allow the systems and methods described herein to selectively display full-color fluorescence images. By displaying full-color fluorescence images as opposed to conventional grayscale fluorescence images, the systems and methods described herein may allow medical personnel (e.g., a surgeon) to more accurately visualize and assess vessels, bile ducts, tissue perfusion, and other anatomical features.

FIG. 1 illustrates an exemplary medical imaging system 100 configured to capture images of a scene. In some examples, the scene may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments being used to perform the surgical procedure are located. In other examples, a surgical area may be at least partially disposed external to the patient.

As shown, medical imaging system 100 includes an imaging device 102 and a controller 104. Medical imaging system 100 may include additional or alternative components as may serve a particular implementation. For example, medical imaging system 100 may include various optical and/or electrical signal transmission components (e.g., wires, lenses, optical fibers, choke circuits, waveguides, etc.), a cable that houses electrical wires and/or optical fibers and that is configured to interconnect imaging device 102 and controller 104, etc.

Imaging device 102 may be implemented by an endoscope or other camera device configured to capture images of a scene. As shown, imaging device 102 includes a camera head 106, a shaft 108 coupled to and extending away from camera head 106, image sensors 110 (i.e., a right-side image sensor 110-R and a left-side image sensor 110-L) at a distal end of shaft 108, and an illumination channel 112. In the example of FIG. 1, imaging device 102 is stereoscopic. Alternatively, in other examples imaging device 102 may be monoscopic (e.g., by including one image sensor 110 instead of two image sensors 110).

Imaging device 102 may be manually handled and controlled (e.g., by a surgeon performing a surgical procedure on a patient). Alternatively, camera head 106 may be coupled to a manipulator arm of a computer-assisted surgical system, an example of which will be provided below. In this configuration, imaging device 102 may be controlled using robotic and/or teleoperation technology.

The distal end of shaft 108 may be positioned at or near a scene that is to be imaged by imaging device 102. For example, the distal end of shaft 108 may be inserted into a patient. In this configuration, imaging device 102 may be used to capture images of anatomy and/or other objects within the patient.

Image sensors 110 may each be implemented by any suitable image sensor, such as a charge coupled device ("CCD") image sensor, a complementary metal-oxide semiconductor ("CMOS") image sensor, or the like. In some examples, as shown in FIG. 1, image sensors 110 are positioned at the distal end of shaft 108. Alternatively, image sensors 110 may be positioned closer to a proximal end of shaft 108, inside camera head 106, or outside imaging device 102 (e.g., inside controller 104). In these alternative configurations, optics (e.g., lenses, optical fibers, etc.) included in shaft 108 and/or camera head 106 may convey light from a scene to image sensors 110.

Image sensors 110 are configured to detect (e.g., capture, collect, sense, or otherwise acquire) light. For example, image sensor 110-R is configured to detect the light from a right-side perspective, and image sensor 110-L is configured to detect the light from a left-side perspective. In the example of FIG. 1, the light detected by image sensors 110 includes visible light that reflects off of an object located within a scene. However, as will be described herein, image sensors 110 may additionally or alternatively detect infrared fluorescence illumination emitted by a fluorescence imaging agent located within the scene. As will be illustrated below, image sensors 110 may convert the detected light into data representative of one or more images. Exemplary implementations of image sensors 110 are described herein.

Illumination channel 112 may be implemented by one or more optical components (e.g., optical fibers, light guides, lenses, etc.). As will be described below, illumination may be provided by way of illumination channel 112 to illuminate a scene.

Controller 104 may be implemented by any suitable combination of hardware and software configured to control and/or interface with imaging device 102. For example, controller 104 may be at least partially implemented by a computing device included in a computer-assisted surgical system.

Controller 104 includes a camera control unit ("CCU") 114 and a visible light illumination source 116. Controller 104 may include additional or alternative components as may serve a particular implementation. For example, controller 104 may include circuitry configured to provide power to components included in imaging device 102. In some examples, CCU 114 and/or visible light illumination source 116 are alternatively included in imaging device 102 (e.g., in camera head 106).

CCU 114 is configured to control various parameters (e.g., activation times, auto exposure, etc.) of image sensors 110. As will be described below, CCU 114 may be further configured to receive and process image data from image sensors 110. While CCU 114 is shown in FIG. 1 to be a single unit, CCU 114 may alternatively be implemented by a first CCU configured to control right-side image sensor 110-R and a second CCU configured to control left-side image sensor 110-L.

Visible light illumination source 116 may be configured to generate and emit visible light 118. Visible light 118 may travel by way of illumination channel 112 to a distal end of shaft 108, where visible light 118 exits to illuminate a scene.

Visible light 118 may include one or more color components. For example, visible light 118 may include white light that includes a full spectrum of color components (e.g., red, green, and blue color components). The red color component has wavelengths between approximately 635 and 700 nanometers ("nm"). The green color component has wavelengths between approximately 520 and 560 nm. The blue color component has wavelengths between approximately 450 and 490 nm.

In some examples, visible light 118 is biased to include more of one color component than another color component. For example, visible light 118 may be blue-biased by including more of the blue color component than the red and green color components.

To capture one or more images of a scene, controller 104 (or any other suitable computing device) may activate visible light illumination source 116 and image sensors 110. While activated, visible light illumination source 116 emits visible light 118, which travels via illumination channel 112 to the scene. Image sensors 110 detect visible light 118 reflected from one or more surfaces in the scene. In cases where visible light 118 includes fluorescence excitation illumination, image sensors 110 may additionally or alternatively detect fluorescence illumination that is elicited by the fluorescence excitation illumination.

Image sensors 110 (and/or other circuitry included in imaging device 102) may convert the detected light into image data 120 representative of one or more images of the scene. For example, image sensor 110-R outputs image data 120-R representative of images captured from a right-side perspective and image sensor 110-L outputs image data 120-L representative of images captured from a left-side perspective. Image data 120 may have any suitable format.

Image data 120 is transmitted from image sensors 110 to CCU 114. Image data 120 may be transmitted by way of any suitable communication link between image sensors 110 and CCU 114. For example, image data 120 may be transmitted by way of wires included in a cable that interconnects imaging device 102 and controller 104.

CCU 114 may process (e.g., packetize and/or format) image data 120 and output processed image data 122 (e.g., processed image data 122-R corresponding to image data 120-R and processed image data 122-L corresponding to image data 120-L). Processed image data 122 may be transmitted to an image processing system, which may prepare processed image data 122 for display on one or more display devices (e.g., in the form of video content and/or one or more still images). For example, the image processing system may, based on image data 122, generate one or more full-color and/or grayscale images for display on one or more display devices.

Figure 2:
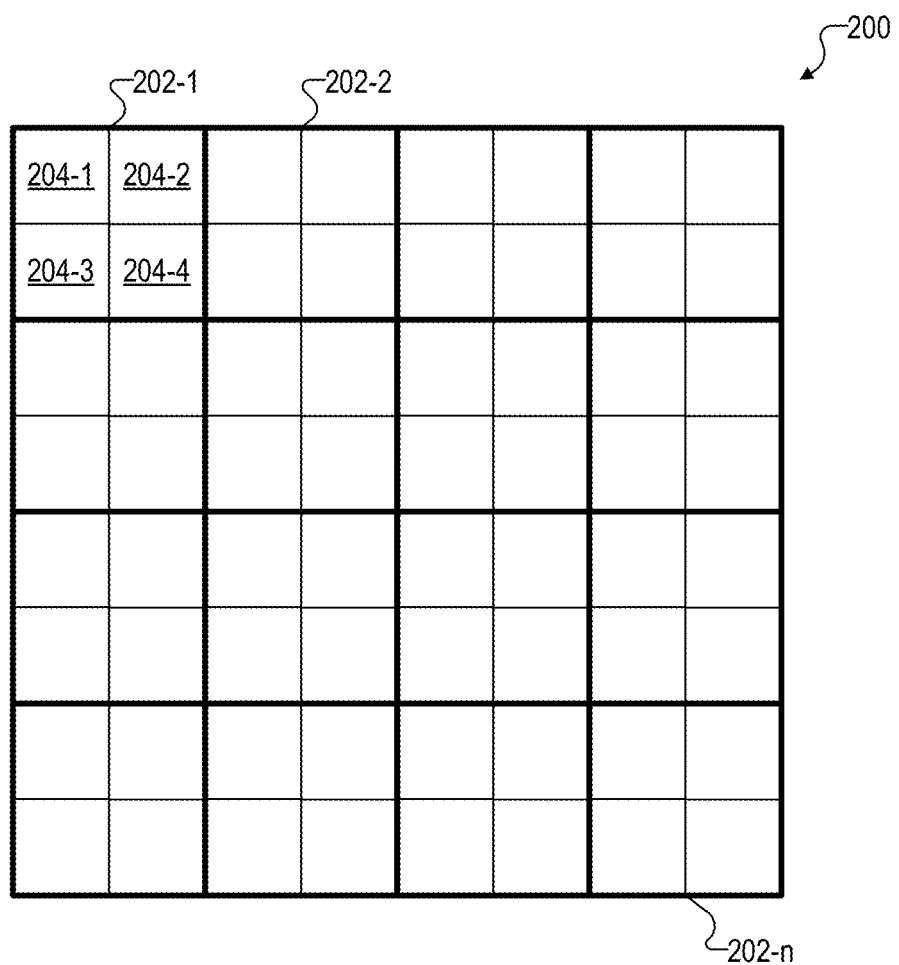
FIG. 2 shows an exemplary image sensor according to principles described herein.

FIG. 2 shows an exemplary image sensor 200. Image sensor 200 may implement image sensors 110 and/or any other image sensor included in an imaging device. As shown, image sensor 200 include a plurality of pixel arrays 202 (e.g., pixel array 202-1 through pixel array 202-n). Each pixel array 202 includes a two-by-two arrangement of pixels 204. For example, pixel array 202-1 includes a first pixel 204-1, a second pixel 204-2, a third pixel 204-3, and a fourth pixel 204-4 arranged as shown in FIG. 2. Image sensor 200 may include any suitable number of pixel arrays 202 as may serve a particular implementation. While two-by-two arrays are shown in FIG. 2, it will be recognized that each array may include any number of pixels 204 (e.g., three-by-three pixel arrays, four-by-four pixel arrays, etc.).

To facilitate color imaging of a scene, image sensor 200 may include an arrangement of color filters that cover pixels 204. Each color filter is configured to allow its corresponding pixel 204 to detect only a particular color component of light incident on pixels 204.

The color filters may cover pixels 204 by being coated on or otherwise adhered to a surface (e.g., a surface upon which light may be incident) of pixels 204. The color filters may alternatively cover pixels 204 in any other suitable manner.

Figure 3A:
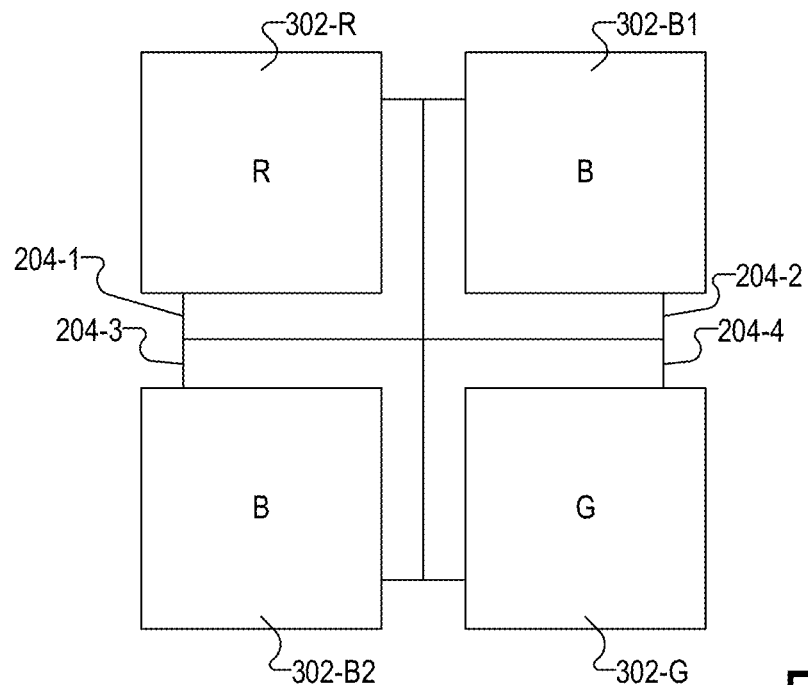
FIGS. 3A-3B show an exemplary color filter arrangement according to principles described herein.
Figure 3B:
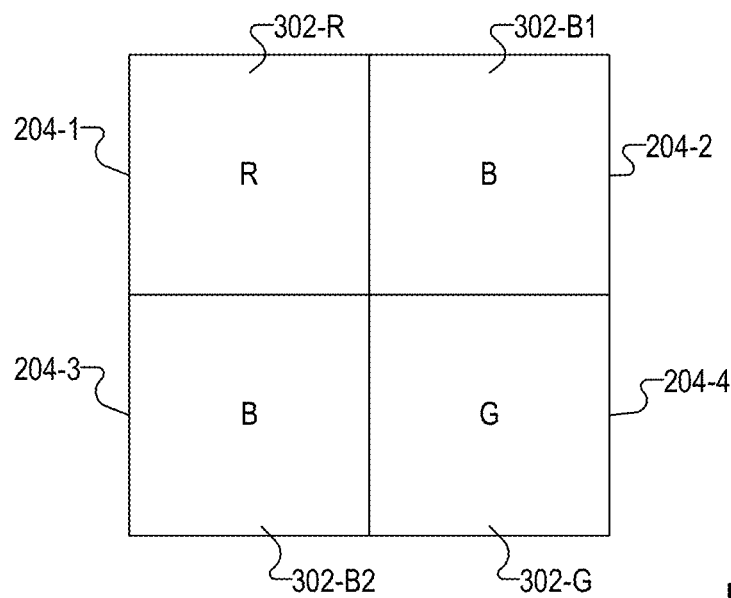

FIGS. 3A-3B show an exemplary color filter arrangement that covers pixels 204 and that may be used in accordance with the systems and methods described herein. As shown, a different color filter 302 may cover each pixel 204. For ease of illustration, FIG. 3A shows filters 302 slightly offset from pixels 204 while FIG. 3B shows filters 302 directly covering pixels 204.

As shown in FIGS. 3A-3B, a red filter 302-R covers pixel 204-1, a first blue filter 302-B1 covers pixel 204-2, a second blue filter 302-B2 covers pixel 204-3, and a green filter 302-G covers pixel 204-4. The filter arrangement shown in FIGS. 3A-3B is referred to herein as an RBBG because of the order in which the color filters 302 are arranged.

Other color filter arrangements that include two blue filters may also be used in accordance with the systems and methods described herein. For example, in an alternative embodiment, first blue filter 302-B1 may cover pixel 204-1, red filter 302-R may cover pixel 204-2, green filter 302-G may cover pixel 204-3, and second blue filter 302-B2 may cover pixel 204-4. This alternative filter arrangement may be referred to as BRBG.

As mentioned, by using a color filter arrangement that is fifty percent blue, such as that shown in FIGS. 3A-3B, the systems and methods described herein may more effectively capture blue-biased light used in medical imaging applications compared to conventional color filter arrangements that are only twenty-five percent blue. Therefore, a color filter arrangement that is fifty percent blue may produce sharper and more accurate images of a surgical area associated with a patient.

In some examples, the color filter arrangements described herein may facilitate other types of imaging that may be useful in medical settings. For example, the color filter arrangements described herein may be used to generate full-color fluorescence images. By displaying full-color fluorescence images as opposed to conventional grayscale fluorescence images, the systems and methods described herein may allow medical personnel (e.g., a surgeon) to more accurately visualize and assess vessels, bile ducts, tissue perfusion, and other anatomical features.

Figure 4:
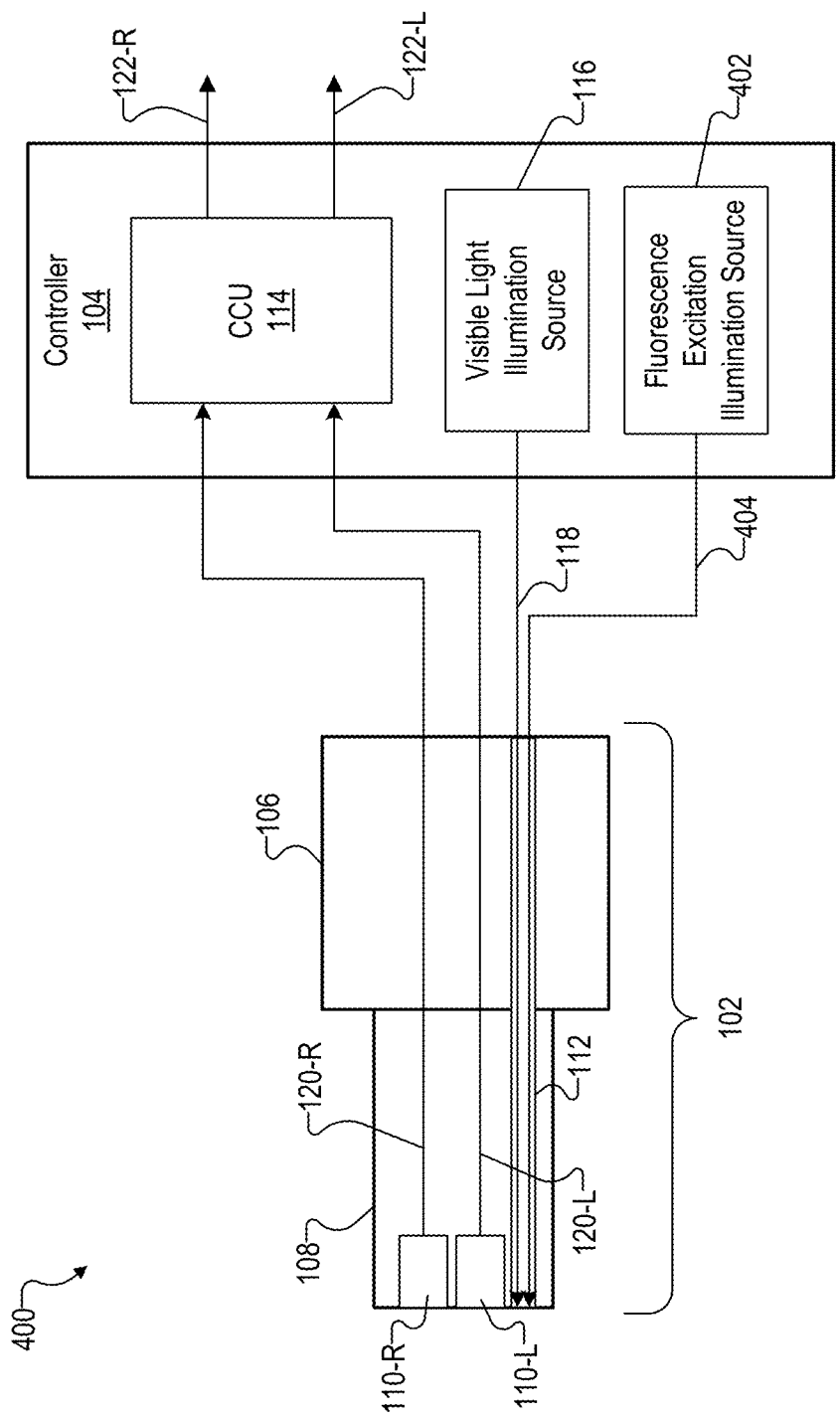
FIG. 4 illustrates an exemplary medical imaging system according to principles described herein.

FIG. 4 shows an exemplary medical imaging system 400 configured to capture fluorescence images in addition to or in combination with color images. Medical imaging system 400 is similar to medical imaging system 100, except that medical imaging system 400 further includes a fluorescence excitation illumination source 402. Fluorescence excitation illumination source 402 is configured to generate and emit fluorescence excitation illumination 404, which may be applied to a scene (e.g., a surgical area associated with a patient) by way of illumination channel 112.

Fluorescence excitation illumination 404 is configured to elicit fluorescence illumination by a fluorescence imaging agent. A fluorescence imaging agent may include any suitable dye, protein, or other substance that may be introduced (e.g., injected) into a bloodstream or other anatomical feature of a patient. When exposed to fluorescence excitation illumination, the fluorescence imaging agent may emit fluorescence illumination (i.e., the fluorescence imaging agent may fluoresce). The fluorescence illumination may be detected by any of the image sensors described herein (e.g., image sensors 110 or image sensor 200) and used to generate fluorescence images that indicate various cellular activity or structures (e.g., blood vasculature in real-time).

In some examples, both the fluorescence excitation illumination and the fluorescence illumination are infrared light. In other words, both the fluorescence excitation illumination and the fluorescence illumination have wavelengths in an infrared light region. The infrared light region includes wavelengths from around 700 nm (the edge of the red visible light region) to around one millimeter. More particularly, both the fluorescence excitation illumination and the fluorescence illumination may have wavelengths included in the near-infrared light region, which is in the infrared light region and includes wavelengths from about 700 nm to about 950 nm. For example, an exemplary fluorescence imaging agent fluoresces at 830 nm when excited by fluorescence excitation illumination that has a wavelength of 803 nm. It will be assumed in the examples herein that both the fluorescence excitation illumination and the fluorescence excitation illumination have wavelengths in the infrared light region.

In some scenarios (e.g., when it is desired to generate a full-color fluorescence image), visible light illumination source 116 and fluorescence excitation illumination source 402 concurrently emit visible light and fluorescence excitation illumination, respectively. In these scenarios, the pixels of image sensors 110 collect both visible light and fluorescence illumination without discriminating between the two types of illumination. Hence, image data 120 output by image sensors 110 includes data representative of both color components and a fluorescence illumination component.

Figure 5:
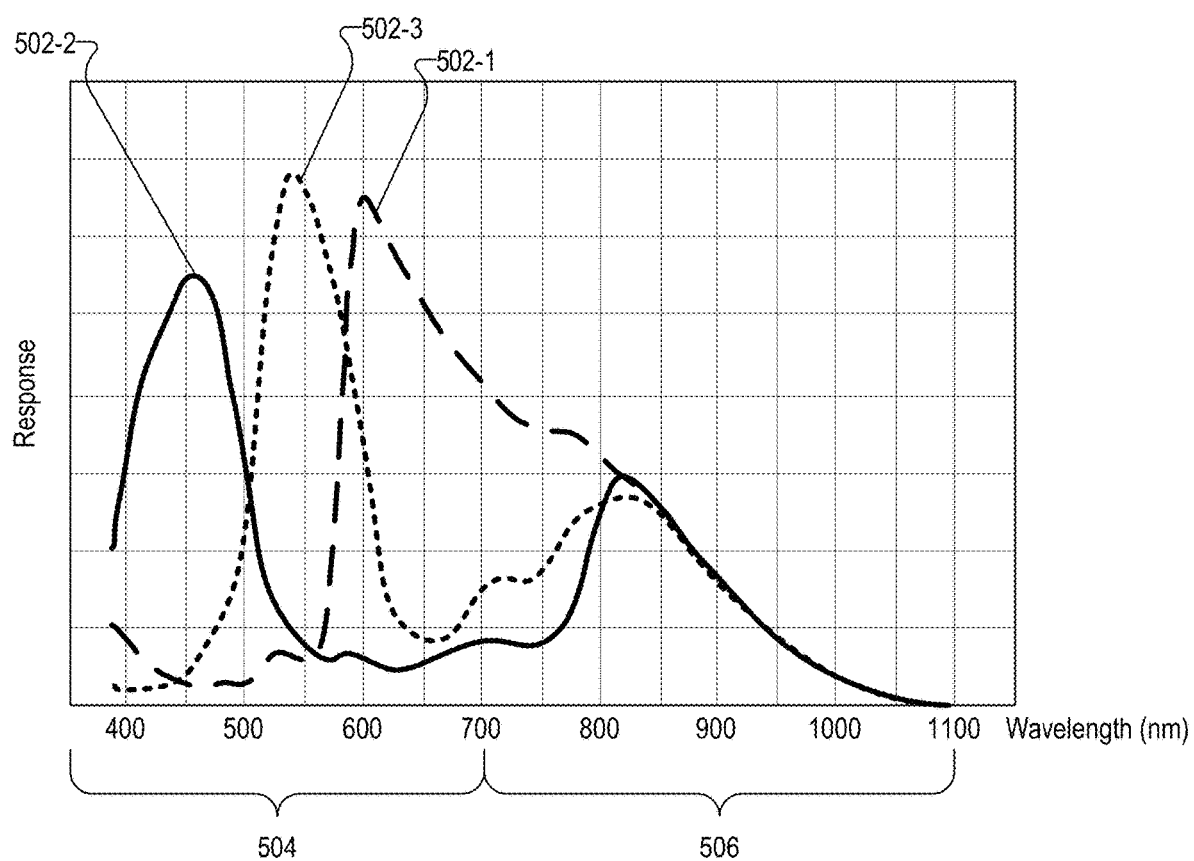
FIG. 5 shows spectral response curves for color filters according to principles described herein.

To illustrate, FIG. 5 shows spectral response curves 502 for color filters 302. For example, FIG. 5 shows a spectral response curve 502-1 for red filter 302-R, a spectral response curve 502-2 for blue filters 302-B1 and 302-B2, and a spectral response curve 502-3 for green filter 302-G. Spectral response curves 502 are represented by different variations of solid and dashed lines to visually distinguish spectral response curves 502 one from another. As shown, spectral response curves 502 are plotted along a horizontal axis that represents wavelengths included in a visible light range 504 and in an infrared light range 506.

Spectral response curves 502 show how each color filter 302 allows its corresponding pixel to collect a particular color component of visible light 118 while preventing the pixel from collecting other color components of visible light 118. For example, spectral response curve 502-1 has a relatively high response at wavelengths in the red color region of visible light range 504 and a relatively low response at wavelengths in other regions of visible light range 504. Hence, red filter 302-R allows pixel 204-1 to collect a red component of visible light 118 while preventing pixel 204-1 from collecting blue and green components of visible light 118. Spectral response curve 502-2 has a relatively high response at wavelengths in the blue color region of visible light range 504 and a relatively low response at wavelengths in other regions of visible light range 504. Hence, blue filters 302-B1 and 302-B2 allow pixels 204-2 and 204-3 to collect a blue component of visible light 118 while preventing pixels 204-2 and 204-3 from collecting red and green components of visible light 118. Spectral response curve 502-3 has a relatively high response at wavelengths in the green color region of visible light range 504 and a relatively low response at wavelengths in other regions of visible light range 504. Hence, green filter 302-G allows pixel 204-4 to collect a green component of visible light 118 while preventing pixel 204-4 from collecting red and blue components of visible light 118.

As also shown in FIG. 5, the spectral response curves 502 each have relatively high responses in infrared light range 506. In other words, each color filter 302 corresponding to spectral response curves 502 does not prevent pixels 204 from collecting at least some types of infrared light. To illustrate, as shown in FIG. 5, color filters 302 may not prevent pixels 204 from collecting near-infrared light.

Hence, in accordance with the systems and methods described herein, one or more infrared cutoff filters may cover one or more of pixels 204 so that an image processing system may distinguish between the color components and the fluorescence illumination component included in image data 122 and thereby direct a display device to display a full-color fluorescence image.

Figure 6A:
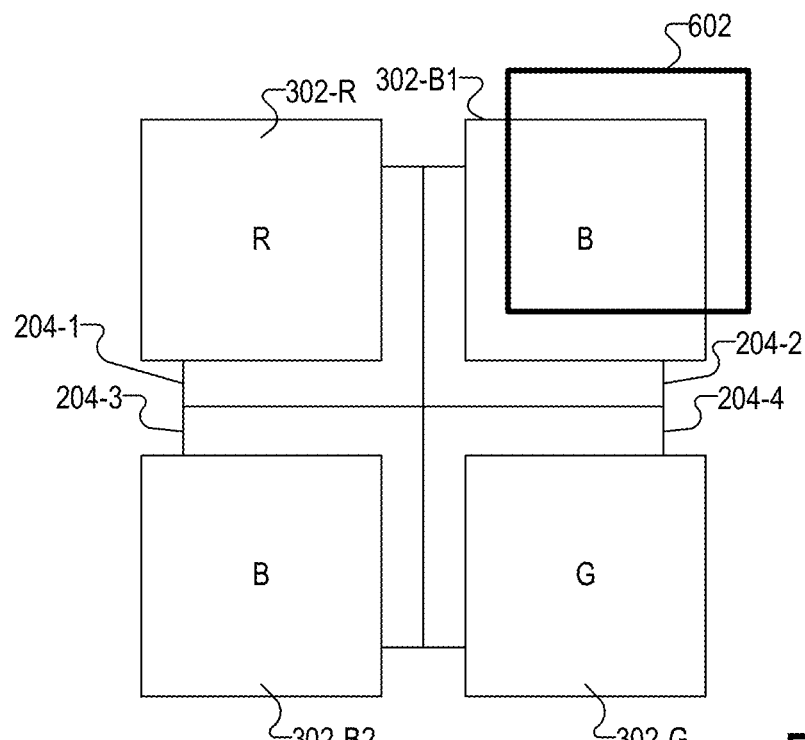
FIGS. 6A-6B illustrate a filter configuration according to principles described herein.
Figure 6B:
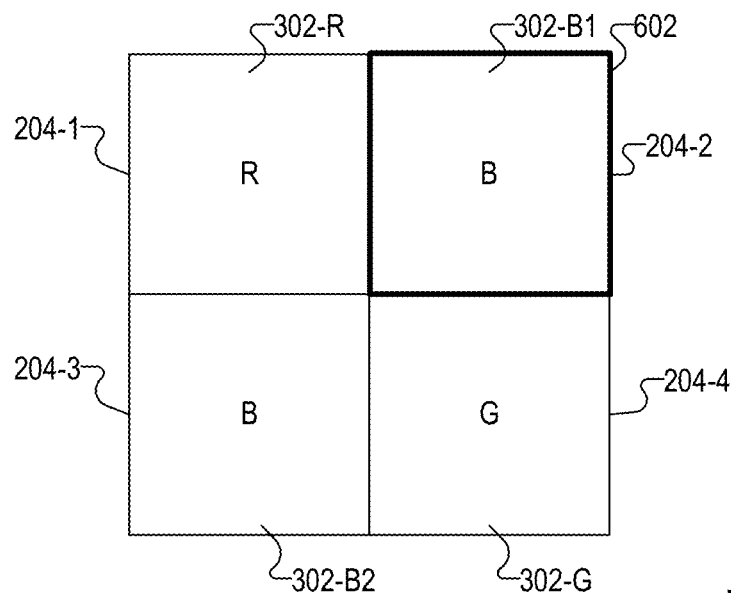

To illustrate, FIGS. 6A-6B illustrate a filter configuration in which a pixel-level broadband infrared cutoff filter 602 ("cutoff filter 602") covers pixel 204-2. Cutoff filter 602 may be implemented by a coating that is configured to adhere to a surface of pixel 204-2 and/or in any other manner.

For ease of illustration, FIG. 6A shows filters 302 and 602 slightly offset from pixels 204 while FIG. 6B shows filters 302 and 602 directly covering pixels 204. Cutoff filter 602 is illustrated in FIGS. 6A-6B as being on top of blue color filter 302-B1. However, in alternative embodiments, blue color filter 302-B1 may be on top of cutoff filter 602.

As shown, pixel-level broadband infrared cutoff filters similar to cutoff filter 602 do not cover pixels 204-1, 204-3, and 204-4. This may advantageously allow an image processing system to distinguish between the color components and the fluorescence illumination component included in image data 122, as will be described below.

Figure 7:
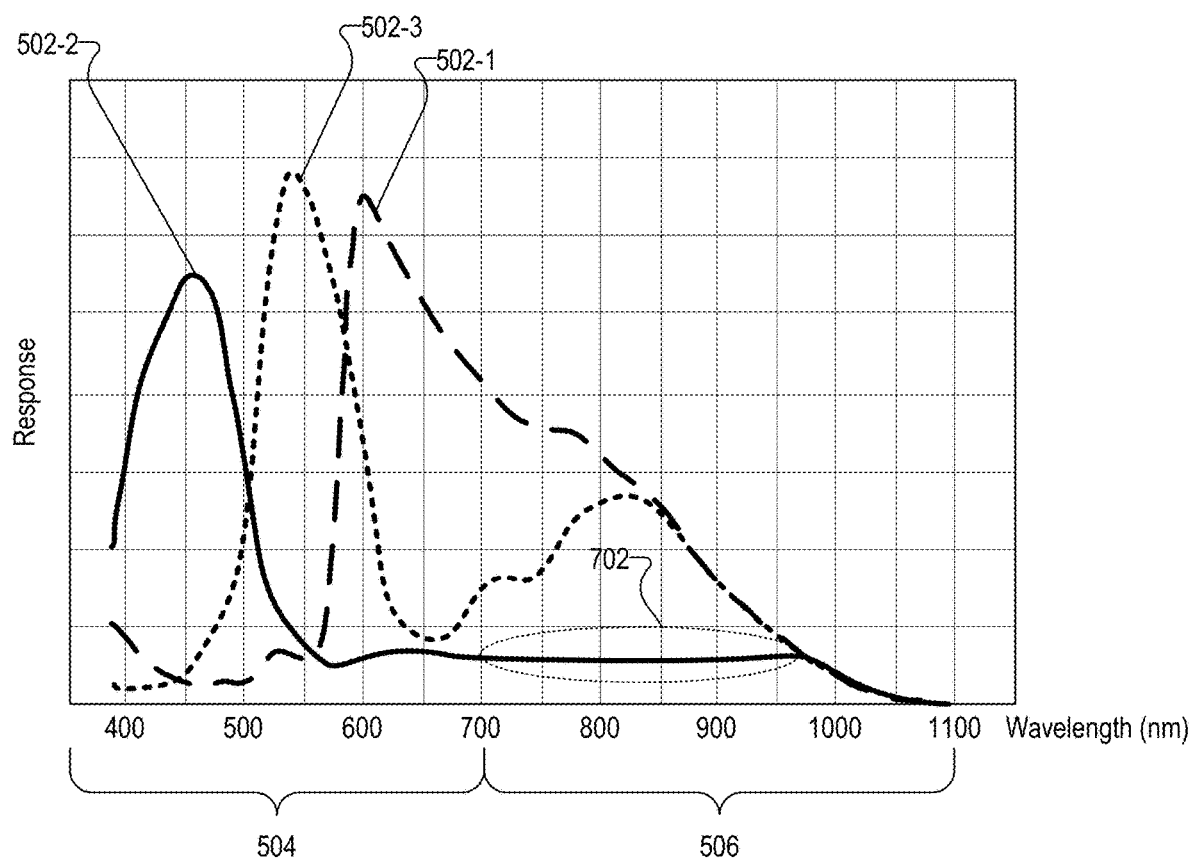
FIG. 7 shows spectral response curves for color filters according to principles described herein.

Cutoff filter 602 is configured to prevent pixel 204-2 from collecting infrared light having wavelengths included in relatively broad range of wavelengths (e.g., the entire near-infrared range). This is illustrated in FIG. 7, which is similar to FIG. 5, except that in FIG. 7 the spectral response 502-2 of color filter 302-2 is relatively flat in the near-infrared range (e.g., between 700 nm and 950 nm). This is highlighted in FIG. 7 by callout 702.

By preventing pixel 204-2 from collecting infrared light, cutoff filter 602 may effectively allow pixel 204-2 to collect only the blue component of visible light 118. In contrast, because pixel 204-3 is not covered by a cutoff filter similar to cutoff filter 602, pixel 204-3 collects both the blue component and the fluorescence illumination elicited by fluorescence excitation illumination 404 when both visible light illumination source 116 and fluorescence excitation illumination source 402 are activated and concurrently emitting light. As will be described below, an image processing system may subtract a signal representative of the light collected by pixel 204-3 from a signal representative of the light collected by pixel 204-2 to identify a fluorescence illumination component included in the signal representative of the light collected by pixel 204-2.

Figure 8A:
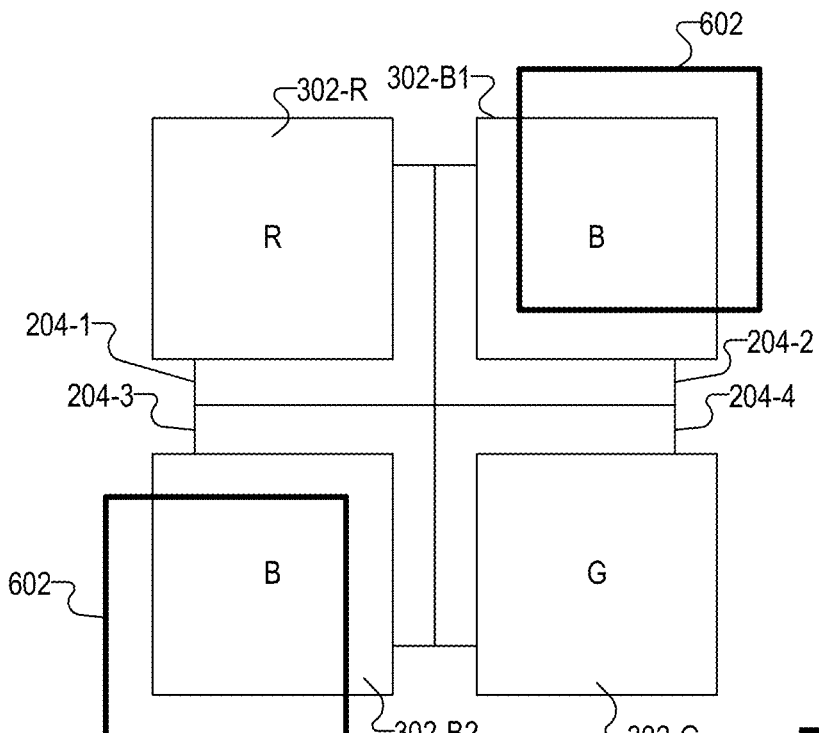
FIGS. 8A-8B, 9A-9B, and 10A-10B illustrate exemplary filter configurations according to principles described herein.
Figure 8B:
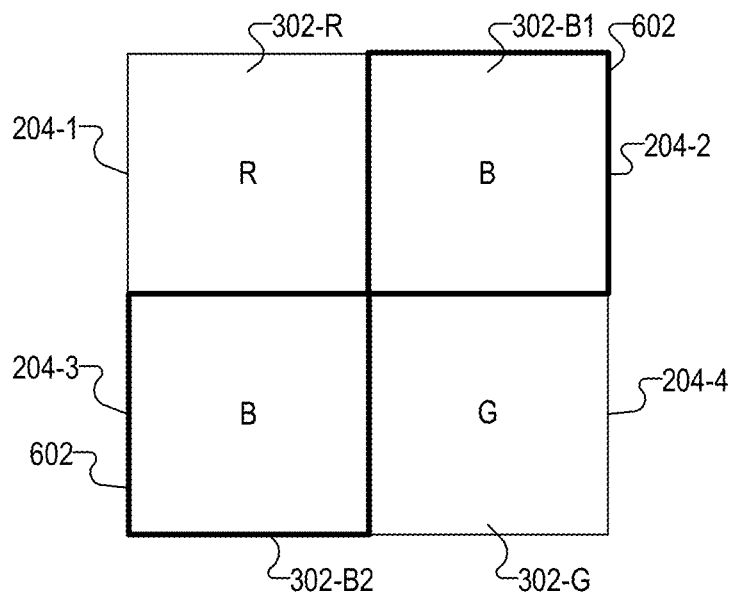

In some alternative embodiments, one or more of pixels 204-1, 204-3, and 204-4 may also be covered by a broadband infrared cutoff filter similar to cutoff filter 602. For example, FIGS. 8A-8B illustrate a filter configuration in which pixel-level broadband infrared cutoff filters 602 cover both pixels 204-2 and 204-3. For ease of illustration, FIG. 8A shows cutoff filters 602 slightly offset from pixels 204-2 and 204-3 while FIG. 8B shows filters 602 directly covering pixels 204-2 and 204-3. The filter configuration of FIGS.

8A-8B may increase the sharpness of color images and grayscale fluorescence images generated based on the light captured by pixels 204.

Figure 9A:
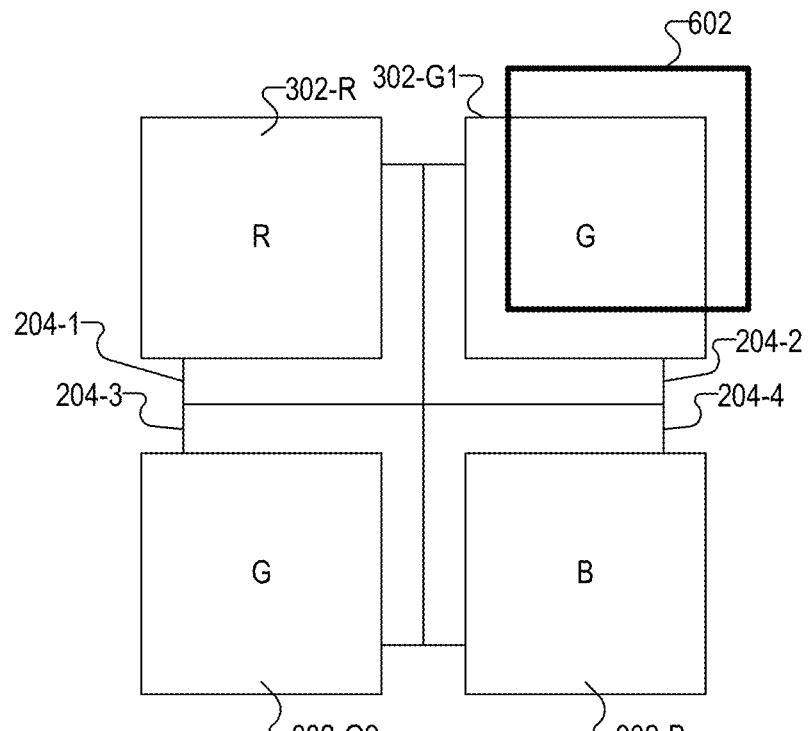
Figure 9B:
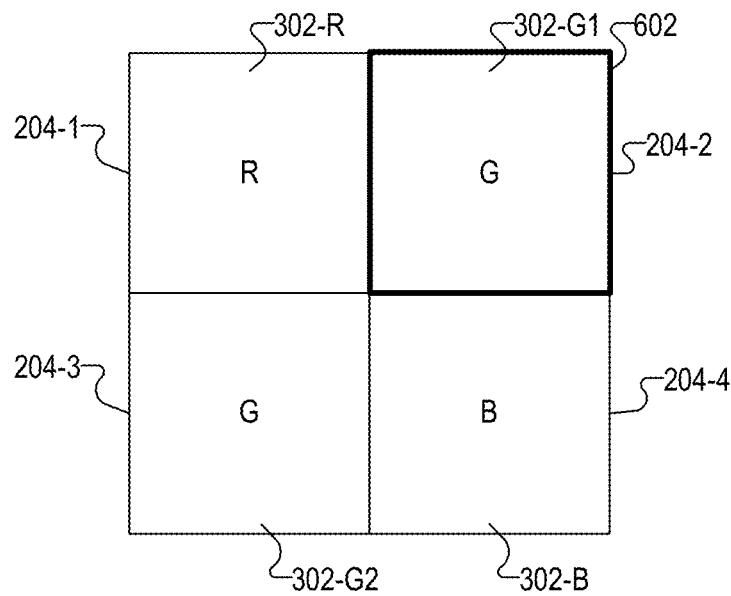

FIGS. 9A-9B show an alternative configuration in which cutoff filter 602 is used in conjunction with an RGGB filter configuration. As shown, red filter 302-R covers pixel 204-1, a first green filter 302-G1 covers pixel 204-2, a second green filter 302-G2 covers pixel 204-3, and a blue filter 302-B covers pixel 204-4. As also shown, cutoff filter 602 also covers pixel 204-2 without similar cutoff filters covering the remaining pixels 204-1, 204-3, and 204-4. For ease of illustration, FIG. 9A shows filters 302 and cutoff filter 602 slightly offset from pixels 204 while FIG. 9B shows filters 302 and cutoff filter 602 directly covering pixels 204. The configuration shown in FIGS. 9A-9B may be used, for example, in imaging applications (e.g., non-medical applications) where the visible light used as illumination is green-biased.

In some examples, a fluorescence imaging agent fluoresces at a different wavelength than fluorescence excitation illumination. For example, as mentioned above, an exemplary fluorescence imaging agent fluoresces at 830 nm when excited by fluorescence excitation illumination that has a wavelength of 803 nm. Because it is desirable to prevent pixels 204 from detecting fluorescence excitation illumination 404 while at the same time allowing at least some of pixels 204 to detect the fluorescence illumination emitted by a fluorescence imaging agent, a narrowband infrared cutoff filter may be further included in the medical imaging systems described herein.

Figure 10A:
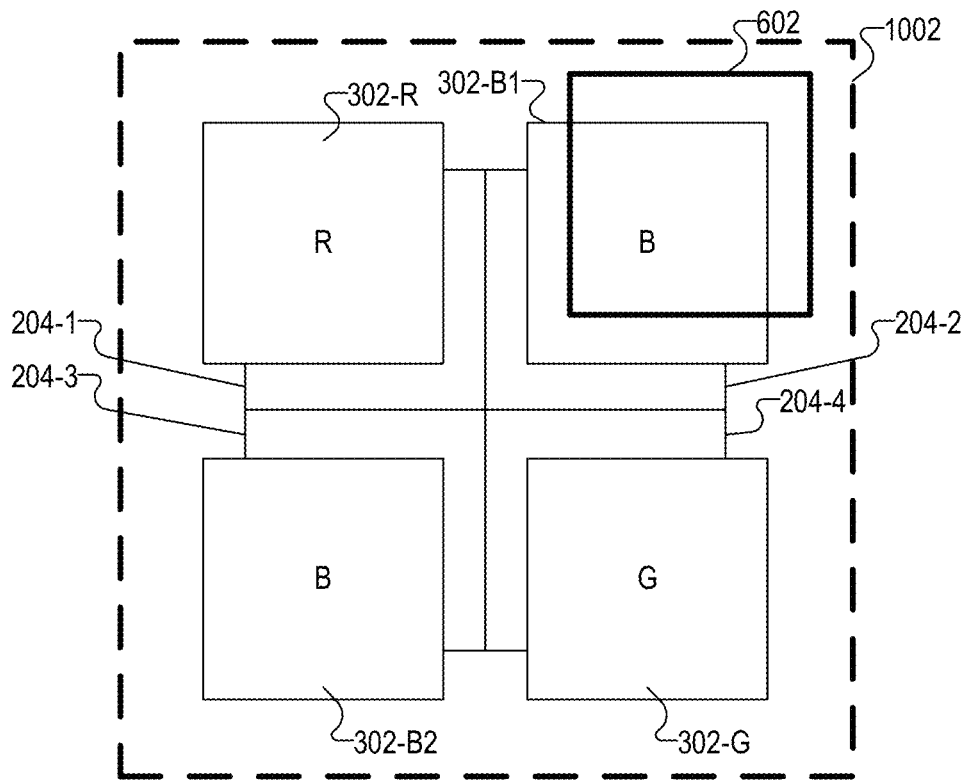

To illustrate, FIG. 10A show an exemplary filter configuration in which a narrowband infrared cutoff filter 1002 covers all of pixels 204. Narrowband infrared cutoff filter 1002 may be implemented as a single glass filter, for example, that covers all of pixels 204 and that is on top of color filters 302 and cutoff filter 602. Narrowband infrared cutoff filter 1002 is configured to prevent pixels 204 from collecting infrared light having a wavelength included in a relatively narrow range of wavelengths (e.g., a range of 20 nm or less) that includes the wavelength of fluorescence excitation illumination 404. As such, narrowband infrared cutoff filter 1002 effectively prevents pixels 204 from detecting fluorescence excitation illumination 404.

Figure 10B:
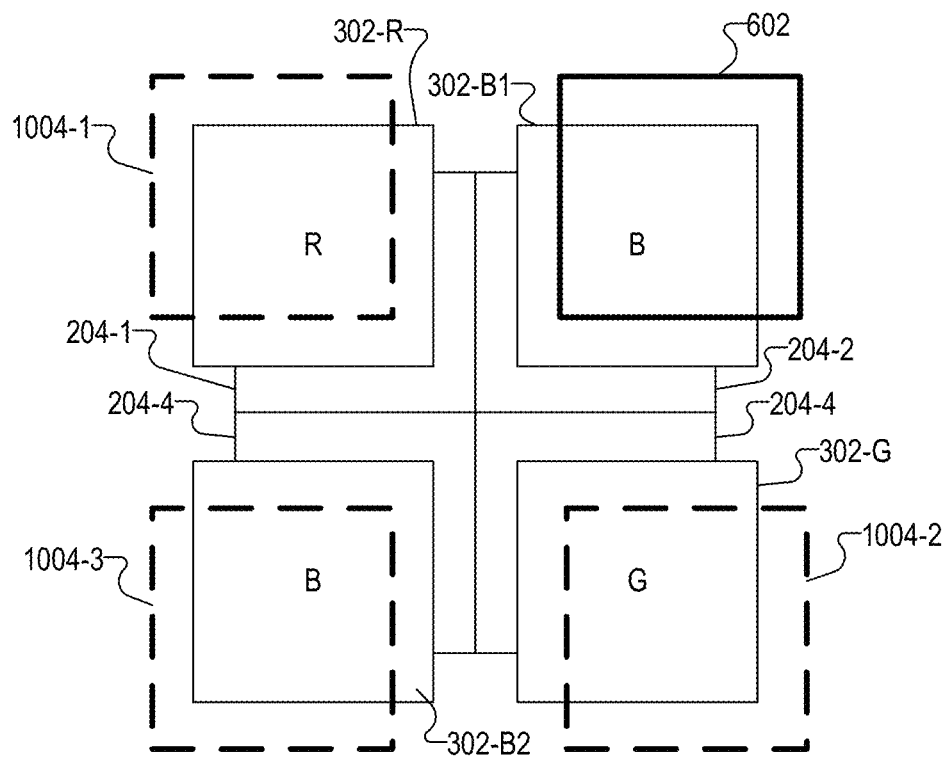

FIG. 10B shows an alternative configuration in which pixel-level narrowband infrared cutoff filters 1004-1, 1004-2, and 1004-3 cover pixels 204-1, 204-3, and 204-4, respectively. Pixel-level narrowband cutoff filters 1004 may be implemented in any suitable manner. Like narrowband infrared cutoff filter 1002, pixel-level narrowband cutoff filters 1004 may effectively prevent pixels 204-1, 204-3, and 204-4 from detecting fluorescence excitation illumination 404. It will be recognized that cutoff filter 602 likewise prevents pixel 204-2 from detecting fluorescence excitation illumination 404 because the wavelength of fluorescence excitation illumination 404 is within the range of wavelengths blocked by cutoff filter 602.

Figure 11:
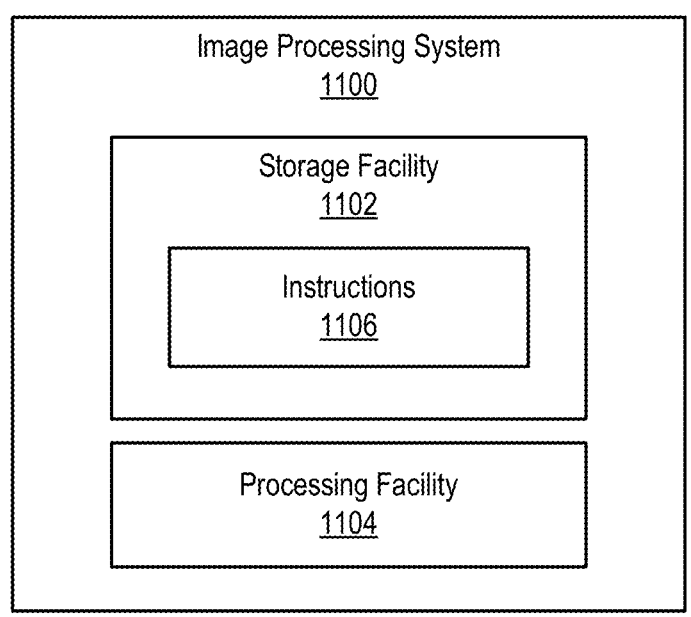
FIG. 11 illustrates an image processing system according to principles described herein.

FIG. 11 illustrates an image processing system 1100 that may be configured to generate, based on signals representative of light collected by pixels 204, one or more images for display on a display device. Image processing system 1100 may be included in or connected to any of the medical imaging systems described herein. For example, in some examples, image processing system 1100 is communicatively coupled to controller 104. In this configuration, image processing system 1100 may receive processed image data 122 as an input.

As shown, system 1100 may include, without limitation, a storage facility 1102 and a processing facility 1104 selectively and communicatively coupled to one another. Facilities 1102 and 1104 may each include or be implemented by hardware and/or software components (e.g., processors, memories, communication interfaces, instructions stored in memory for execution by the processors, etc.). For example, facilities 1102 and 1104 may be implemented by any component in a computer-assisted surgical system. In some examples, facilities 1102 and 1104 may be distributed between multiple devices and/or multiple locations as may serve a particular implementation.

Storage facility 1102 may maintain (e.g., store) executable data used by processing facility 1104 to perform any of the operations described herein. For example, storage facility 1102 may store instructions 1106 that may be executed by processing facility 1104 to perform any of the operations described herein. Instructions 1106 may be implemented by any suitable application, software, code, and/or other executable data instance. Storage facility 1102 may also maintain any data received, generated, managed, used, and/or transmitted by processing facility 1104.

Processing facility 1104 may be configured to perform (e.g., execute instructions 1106 stored in storage facility 1102 to perform) various operations associated with generating images for display on a display device.

For example, processing facility 1104 may activate visible light illumination source 116 and fluorescence excitation illumination source 402 to concurrently emit visible light 118 and fluorescence excitation illumination 404. While visible light 118 and fluorescence excitation illumination 404 are being concurrently emitted (or, alternatively, after visible light 118 and fluorescence excitation illumination 404 have been emitted), processing facility 1104 may receive a first signal $S_1$ representative of light collected by pixel 204-1, a second signal $S_2$ representative of light collected by pixel 204-2, a third signal $S_3$ representative of light collected by pixel 204-3, and a fourth signal $S_4$ representative of light collected by pixel 204-4.

In this example, pixels 204 are covered by the filter arrangement shown in FIG. 10A or FIG. 10B (i.e., an RBBG color filter arrangement with cutoff filter 602 covering pixel 204-2 and narrowband infrared cutoff filter 1002 or narrowband infrared cutoff filters 1004 covering the remaining pixels 204-1, 204-3, and 204-4). It will also be assumed for purposes of this example that the fluorescence excitation illumination 404 has a wavelength of 803 nm and that the fluorescence illumination elicited by fluorescence excitation illumination 404 has a wavelength of 830 nm.

Hence, the signals received by processing facility 1104 may be represented by the following equations:

$$S_1 = R + FI$$
$$S_2 = B$$
$$S_3 = B + FI$$
$$S_4 = G + FI$$

In these equations, R represents the red component of the light captured by pixel 204-1, B represents the blue component of the light captured by pixels 204-2 and 204-3, G represents the green component of the light captured by pixel 204-4, and FI represents the fluorescence illumination captured by pixels 204-1, 204-3, and 204-4. Note that none of the signals $S_1$ through $S_4$ includes the fluorescence excitation illumination 404 due to the presence of cutoff filter 602 covering pixel 204-2 and narrowband infrared cutoff filter 1002 or narrowband infrared cutoff filters 1004 covering the pixels 204-1, 204-3, and 204-4.

Figure 12:
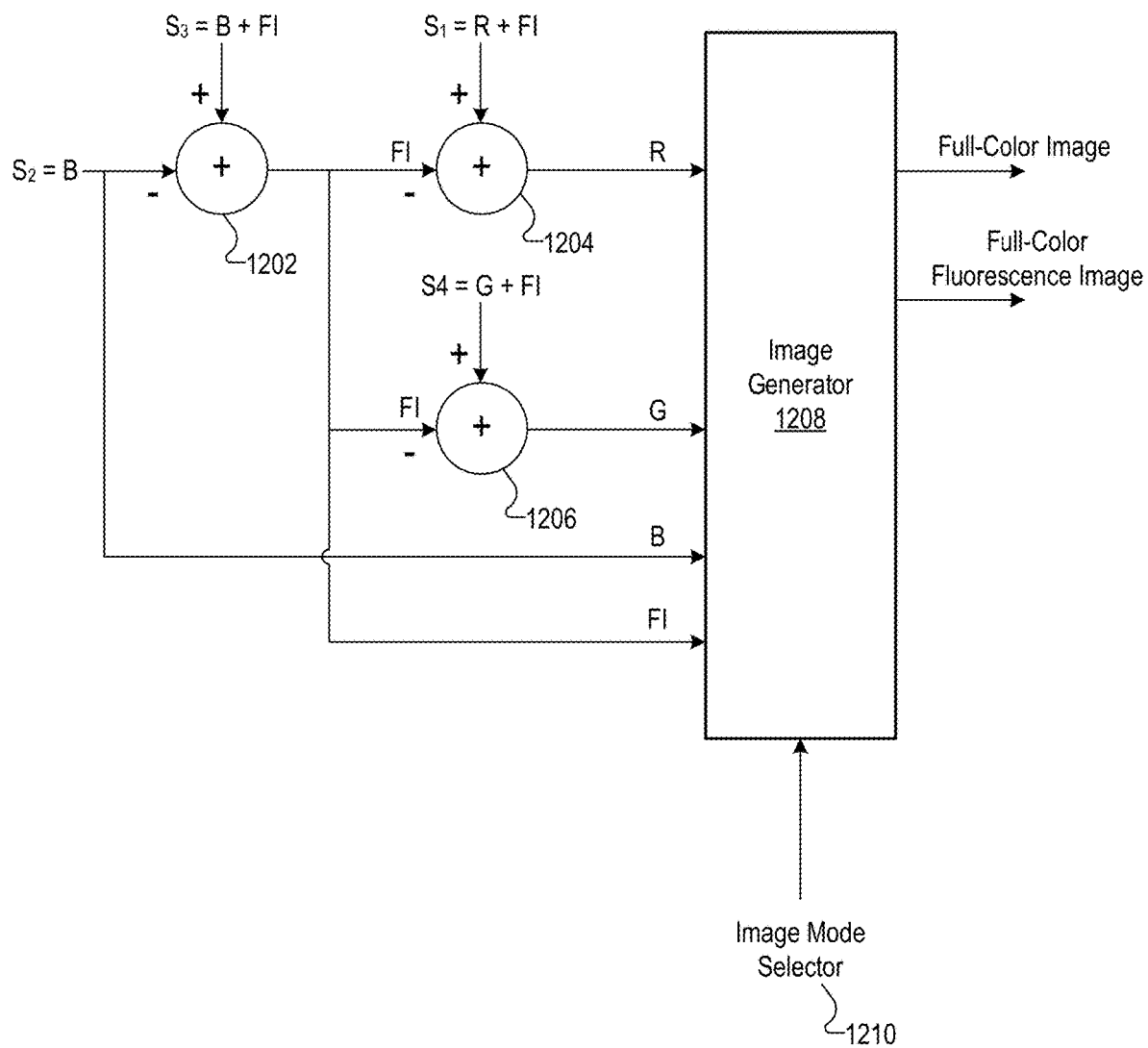
FIG. 12 shows various operations that may be performed by an imaging processing system to selectively generate a full-color image and a full-color fluorescence image according to principles described herein.

Processing facility 1104 may process signals $S_1$ through $S_4$ to selectively generate a full-color image (without fluorescence) and a full-color fluorescence image. For example, FIG. 12 shows various operations that may be performed by processing facility 1104 to selectively generate a full-color image and a full-color fluorescence image.

At summing block 1202, processing facility 1104 first subtracts $S_2$ from $S_3$ to identify a fluorescence illumination component FI included in $S_3$. This subtraction may be performed using any suitable signal processing operation.

To identify the red component R and the green component G, processing facility 1104 subtracts FI from $S_1$ at summing block 1204 and FI from $S_4$ at summing block 1206. As shown, the output of summing block 1204 is a processed first signal representative of only the red component R and the output of summing block 1206 is a processed fourth signal representative of only the green component G.

As shown, R, G, B, and FI are all input into an image generator 1208, which may be implemented by processing facility 1104 in any suitable manner. Image generator 1208 may generate, based on a received image mode selector command 1210, various types of images for display by a display device. Image mode selector command 1210 may be provided by a user (e.g., a surgeon), by any component included in a computer-assisted surgical system, and/or by any other source as may serve a particular implementation. Image mode selector command 1210 may be received by image generator 1208 while visible light 118 and fluorescence excitation illumination 404 are concurrently being emitted and/or at any other suitable time.

To illustrate, image mode selector command 1210 may include a command to present a full-color image that does not include fluorescence image. In response to receiving this command, image generator 1208 may generate the full-color image based on the R, G, and B signals using any suitable image processing technique.

Alternatively, if image mode selector command 1210 includes a command to present a full-color fluorescence image, image generator 1208 may generate the full-color fluorescence image based on the R, G, B, and IR signals. This may be performed using any suitable image processing technique.

Figure 13:
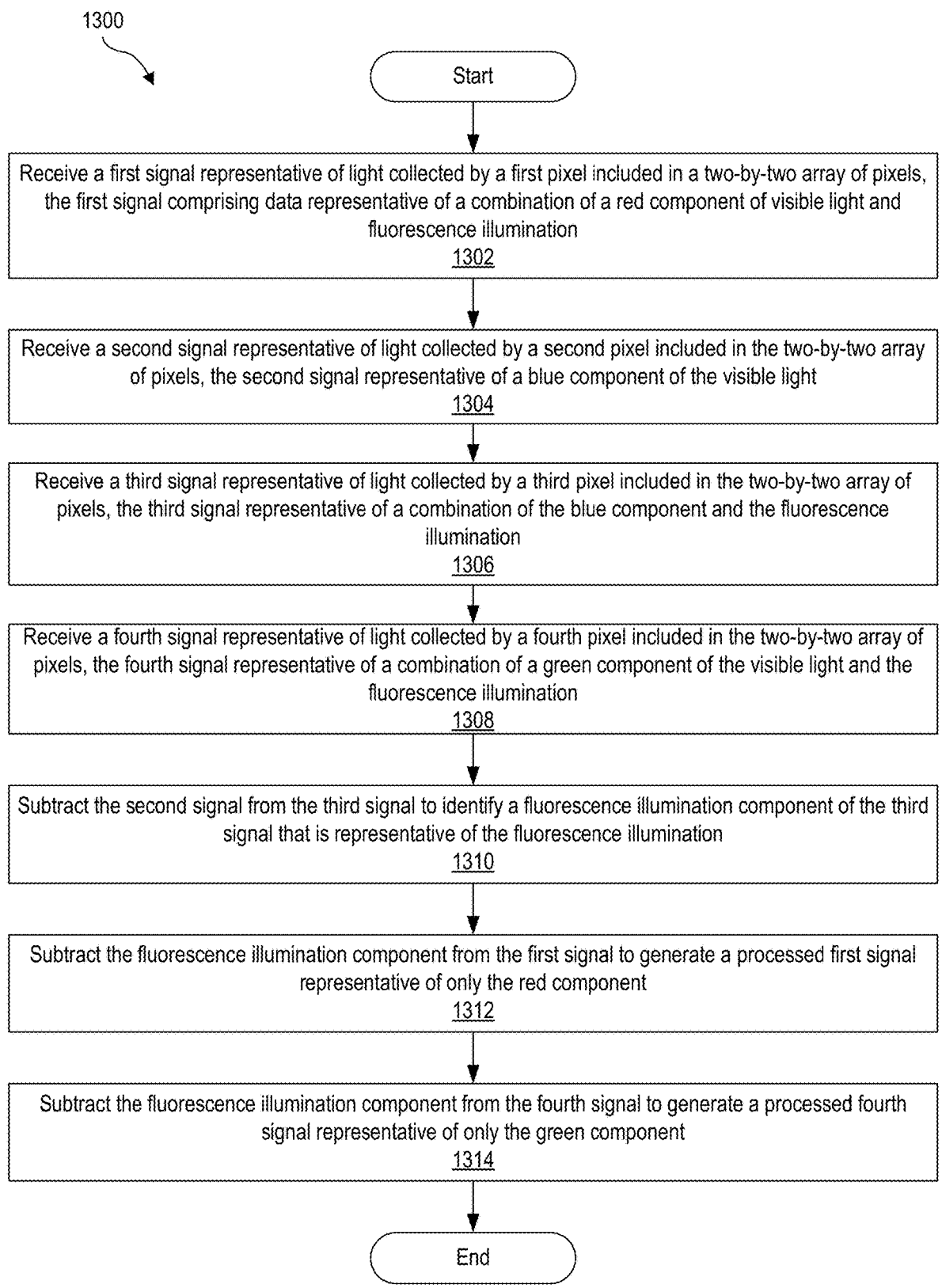
FIG. 13 illustrates an exemplary method according to principles described herein.

FIG. 13 illustrates an exemplary method 1300 that may be performed by image processing system 1100. While FIG. 13 illustrates exemplary operations according to one embodiment, other embodiments may omit, add to, reorder, and/or modify any of the operations shown in FIG. 13.

In operation 1302, image processing system 1100 receive a first signal representative of light collected by a first pixel included in a two-by-two array of pixels, the first signal comprising data representative of a combination of a red component of visible light and fluorescence illumination. Operation 1302 may be performed in any of the ways described herein.

In operation 1304, image processing system 1100 receives a second signal representative of light collected by a second pixel included in the two-by-two array of pixels, the second signal representative of a blue component of the visible light. Operation 1304 may be performed in any of the ways described herein.

In operation 1306, image processing system 1100 receives a third signal representative of light collected by a third pixel included in the two-by-two array of pixels, the third signal representative of a combination of the blue component and the fluorescence illumination. Operation 1306 may be performed in any of the ways described herein.

In operation 1308, image processing system 1100 receives a fourth signal representative of light collected by a fourth pixel included in the two-by-two array of pixels, the fourth signal representative of a combination of a green component of the visible light and the fluorescence illumination. Operation 1308 may be performed in any of the ways described herein.

In operation 1310, image processing system 1100 subtracts the second signal from the third signal to identify a fluorescence illumination component of the third signal that is representative of the fluorescence illumination. Operation 1310 may be performed in any of the ways described herein.

In operation 1312, image processing system 1100 subtracts the fluorescence illumination component from the first signal to generate a processed first signal representative of only the red component. Operation 1312 may be performed in any of the ways described herein.

In operation 1314, image processing system 1100 subtracts the fluorescence illumination component from the fourth signal to generate a processed fourth signal representative of only the green component. Operation 1314 may be performed in any of the ways described herein.

The systems and methods described herein may be used in connection with a computer-assisted surgical system used to perform a surgical procedure with respect to a patient. For example, medical imaging systems 100 and 400 may be included in a computer-assisted surgical system.

Figure 14:
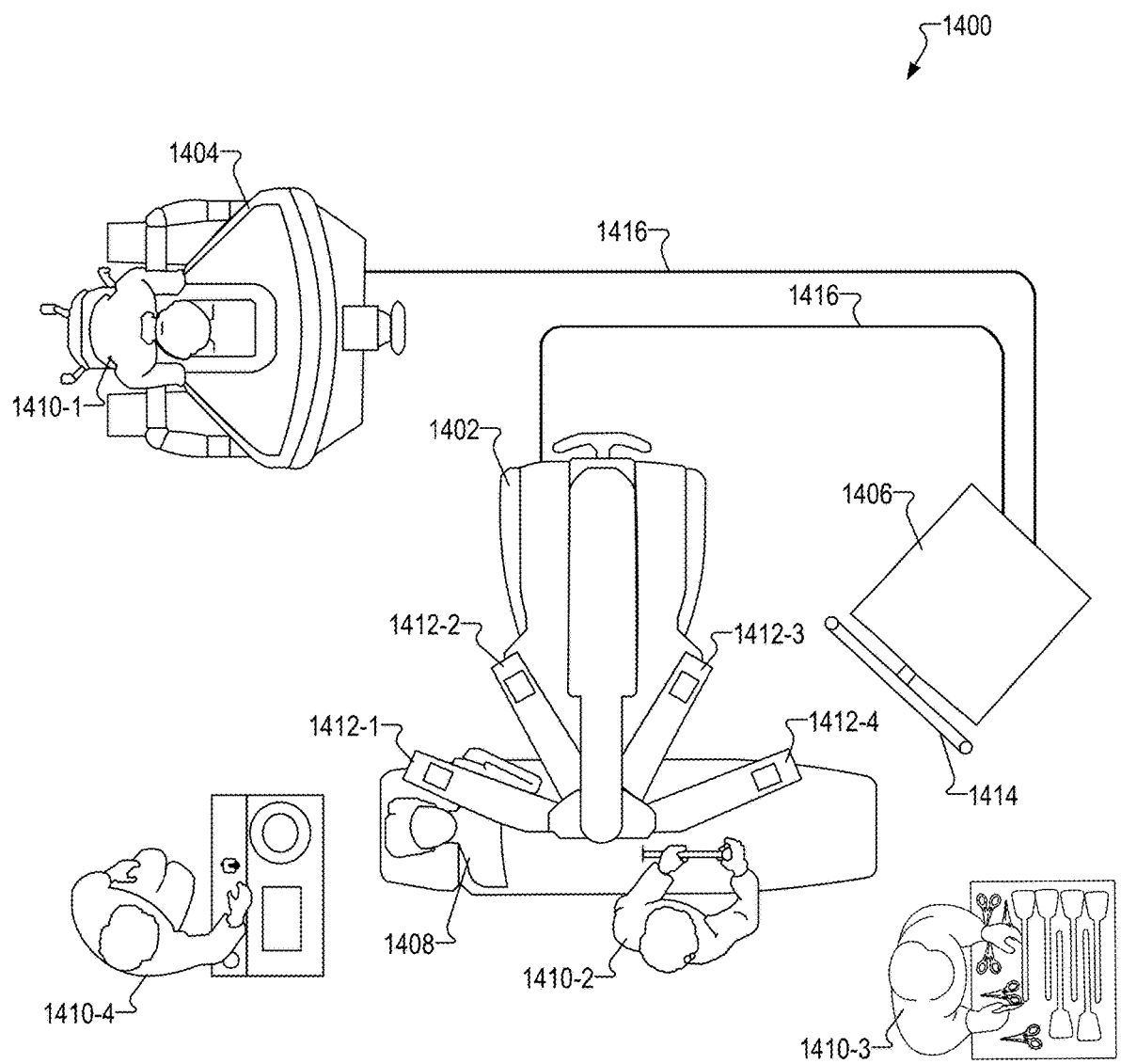
FIG. 14 illustrates an exemplary computer-assisted surgical system according to principles described herein.

FIG. 14 illustrates an exemplary computer-assisted surgical system 1400 ("surgical system 1400"). As shown, surgical system 1400 may include a manipulating system 1402, a user control system 1404, and an auxiliary system 1406 communicatively coupled one to another. Surgical system 1400 may be utilized by a surgical team to perform a computer-assisted surgical procedure on a patient 1408. As shown, the surgical team may include a surgeon 1410-1, an assistant 1410-2, a nurse 1410-3, and an anesthesiologist 1410-4, all of whom may be collectively referred to as "surgical team members 1410." Additional or alternative surgical team members may be present during a surgical session as may serve a particular implementation.

While FIG. 14 illustrates an ongoing minimally invasive surgical procedure, it will be understood that surgical system 1400 may similarly be used to perform open surgical procedures or other types of surgical procedures that may similarly benefit from the accuracy and convenience of surgical system 1400. Additionally, it will be understood that the surgical session throughout which surgical system 1400 may be employed may not only include an operative phase of a surgical procedure, as is illustrated in FIG. 14, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 14, manipulating system 1402 may include a plurality of manipulator arms 1412 (e.g., manipulator arms 1412-1 through 1412-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 1408 (e.g., by being at least partially inserted into patient 1408 and manipulated to perform a computer-assisted surgical procedure on patient 1408). While manipulating system 1402 is depicted and described herein as including four manipulator arms 1412, it will be recognized that manipulating system 1402 may include only a single manipulator arm 1412 or any other number of manipulator arms as may serve a particular implementation.

Manipulator arms 1412 and/or surgical instruments attached to manipulator arms 1412 may include one or more displacement transducers, orientational sensors, and/or positional sensors used to generate raw (i.e., uncorrected) kinematics information. One or more components of surgical system 1400 may be configured to use the kinematics information to track (e.g., determine positions of) and/or control the surgical instruments.

User control system 1404 may be configured to facilitate control by surgeon 1410-1 of manipulator arms 1412 and surgical instruments attached to manipulator arms 1412. For example, surgeon 1410-1 may interact with user control system 1404 to remotely move or manipulate manipulator arms 1412 and the surgical instruments. To this end, user control system 1404 may provide surgeon 1410-1 with imagery (e.g., high-definition 3D imagery) of a surgical area associated with patient 1408 as captured by an imaging system (e.g., any of the medical imaging systems described herein). In certain examples, user control system 1404 may include a stereo viewer having two displays where stereoscopic images of a surgical area associated with patient 1408 and generated by a stereoscopic imaging system may be viewed by surgeon 1410-1. Surgeon 1410-1 may utilize the imagery to perform one or more procedures with one or more surgical instruments attached to manipulator arms 1412.

To facilitate control of surgical instruments, user control system 1404 may include a set of master controls. These master controls may be manipulated by surgeon 1410-1 to control movement of surgical instruments (e.g., by utilizing robotic and/or teleoperation technology). The master controls may be configured to detect a wide variety of hand, wrist, and finger movements by surgeon 1410-1. In this manner, surgeon 1410-1 may intuitively perform a procedure using one or more surgical instruments.

Auxiliary system 1406 may include one or more computing devices configured to perform primary processing operations of surgical system 1400. In such configurations, the one or more computing devices included in auxiliary system 1406 may control and/or coordinate operations performed by various other components (e.g., manipulating system 1402 and user control system 1404) of surgical system 1400. For example, a computing device included in user control system 1404 may transmit instructions to manipulating system 1402 by way of the one or more computing devices included in auxiliary system 1406. As another example, auxiliary system 1406 may receive, from manipulating system 1402, and process image data representative of imagery captured by an imaging device attached to one of manipulator arms 1412.

In some examples, auxiliary system 1406 may be configured to present visual content to surgical team members 1410 who may not have access to the images provided to surgeon 1410-1 at user control system 1404. To this end, auxiliary system 1406 may include a display monitor 1414 configured to display one or more user interfaces, such as images (e.g., 2D images) of the surgical area, information associated with patient 1408 and/or the surgical procedure, and/or any other visual content as may serve a particular implementation. For example, display monitor 1414 may display images of the surgical area together with additional content (e.g., graphical content, contextual information, etc.) concurrently displayed with the images. In some embodiments, display monitor 1414 is implemented by a touchscreen display with which surgical team members 1410 may interact (e.g., by way of touch gestures) to provide user input to surgical system 1400.

Manipulating system 1402, user control system 1404, and auxiliary system 1406 may be communicatively coupled one to another in any suitable manner. For example, as shown in FIG. 14, manipulating system 1402, user control system 1404, and auxiliary system 1406 may be communicatively coupled by way of control lines 1416, which may represent any wired or wireless communication link as may serve a particular implementation. To this end, manipulating system 1402, user control system 1404, and auxiliary system 1406 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 15:
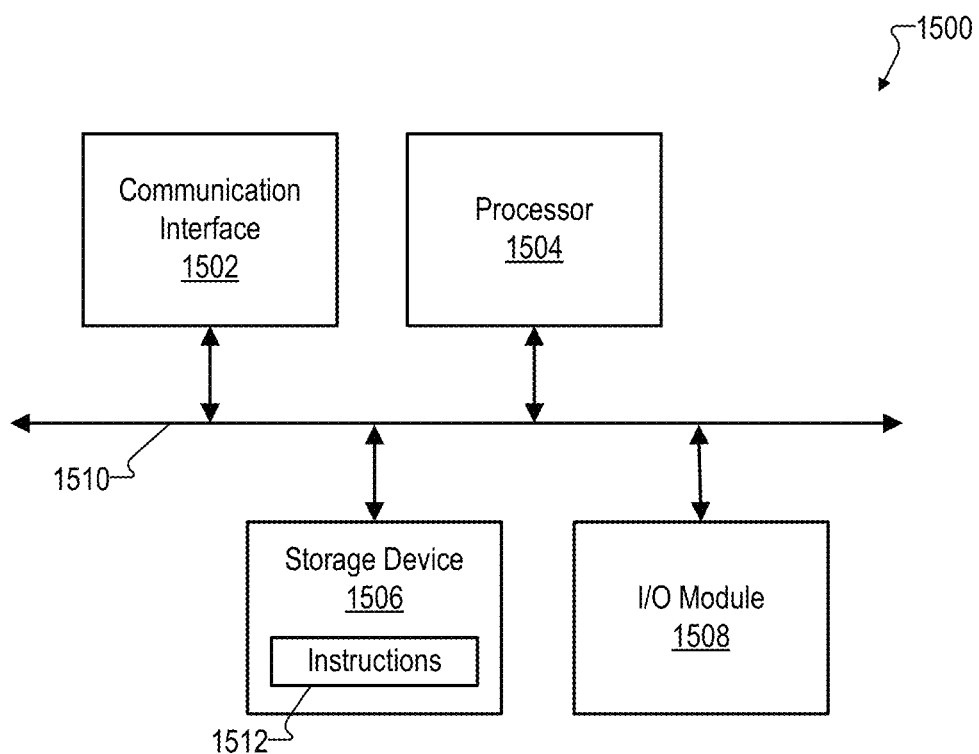
FIG. 15 illustrates an exemplary computing device according to principles described herein.

FIG. 15 illustrates an exemplary computing device 1500 that may be specifically configured to perform one or more of the processes described herein. Any of the systems, computing devices, and/or other components described herein may be implemented by computing device 1500.

As shown in FIG. 15, computing device 1500 may include a communication interface 1502, a processor 1504, a storage device 1506, and an input/output ("I/O") module 1508 communicatively connected one to another via a communication infrastructure 1510. While an exemplary computing device 1500 is shown in FIG. 15, the components illustrated in FIG. 15 are not intended to be limiting. Additional or alternative components may be used in other embodiments. Components of computing device 1500 shown in FIG. 15 will now be described in additional detail.

Communication interface 1502 may be configured to communicate with one or more computing devices. Examples of communication interface 1502 include, without limitation, a wired network interface (such as a network interface card), a wireless network interface (such as a wireless network interface card), a modem, an audio/video connection, and any other suitable interface.

Processor 1504 generally represents any type or form of processing unit capable of processing data and/or interpreting, executing, and/or directing execution of one or more of the instructions, processes, and/or operations described herein. Processor 1504 may perform operations by executing computer-executable instructions 1512 (e.g., an application, software, code, and/or other executable data instance) stored in storage device 1506.

Storage device 1506 may include one or more data storage media, devices, or configurations and may employ any type, form, and combination of data storage media and/or device. For example, storage device 1506 may include, but is not limited to, any combination of the non-volatile media and/or volatile media described herein. Electronic data, including data described herein, may be temporarily and/or permanently stored in storage device 1506. For example, data representative of computer-executable instructions 1512 configured to direct processor 1504 to perform any of the operations described herein may be stored within storage device 1506. In some examples, data may be arranged in one or more databases residing within storage device 1506.

I/O module 1508 may include one or more I/O modules configured to receive user input and provide user output. I/O module 1508 may include any hardware, firmware, software, or combination thereof supportive of input and output capabilities. For example, I/O module 1508 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1508 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1508 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   an image sensor comprising a first pixel, a second pixel, a third pixel, and a fourth pixel; and
   a pixel-level broadband infrared cutoff filter that covers the second pixel and that is configured to prevent the second pixel from collecting infrared light having wavelengths included in a first range of wavelengths;
   wherein the first, third, and fourth pixels are not covered by pixel-level broadband infrared cutoff filters configured to prevent the first, third, and fourth pixels from collecting infrared light having wavelengths included in the first range of wavelengths; and
   wherein the system further comprises a narrowband infrared cutoff filter that covers the first, third, and fourth pixels and that is configured to prevent the first, third, and fourth pixels from collecting infrared light having a wavelength included in a second range of wavelengths, the second range of wavelengths included in and narrower than the first range of wavelengths.

2. The system of claim 1, wherein the narrowband infrared cutoff filter comprises a glass filter that covers the first, second, third, and fourth pixels.

3. The system of claim 1, wherein the narrowband infrared cutoff filter comprises:
   a first pixel-level narrowband infrared cutoff filter that covers the first pixel;
   a second pixel-level narrowband infrared cutoff filter that covers the third pixel; and
   a third pixel-level narrowband infrared cutoff filter that covers the fourth pixel.

4. The system of claim 1, further comprising:
   a visible light illumination source configured to illuminate a scene with visible light, the first pixel collecting a first color component of the visible light after the visible light reflects from one or more surfaces in the scene, the second and third pixels each collecting a second color component of the visible light after the visible light reflects from the one or more surfaces in the scene, and the fourth pixel collecting a third color component of the visible light after the visible light reflects from the one or more surfaces in the scene; and
   a fluorescence excitation illumination source configured to emit fluorescence excitation illumination that elicits fluorescence illumination by a fluorescence imaging agent.

5. The system of claim 4, wherein:
   the fluorescence excitation illumination has a wavelength included in the second range of wavelengths such that the pixel-level broadband infrared cutoff filter and the narrowband infrared cutoff filter prevent the first, second, third, and fourth pixels from collecting the fluorescence excitation illumination; and
   the fluorescence illumination has a wavelength included in the first range of wavelengths but not included in the second range of wavelengths such that the pixel-level broadband infrared cutoff filter prevents the second pixel from collecting the fluorescence illumination while the narrowband infrared cutoff filter allows the first, third, and fourth pixels to collect the fluorescence illumination.

6. The system of claim 5, further comprising an image processing system configured to:
   activate the visible light illumination source and the fluorescence excitation illumination source to concurrently emit the visible light and the fluorescence excitation illumination, and
   while the visible light and the fluorescence excitation illumination are concurrently being emitted,
      receive a first signal representative of light collected by the first pixel, the first signal comprising data representative of a combination of the first color component and the fluorescence illumination,
      receive a second signal representative of light collected by the second pixel, the second signal representative of the second color component,
      receive a third signal representative of light collected by the third pixel, the third signal representative of a combination of the second color component and the fluorescence illumination, and receive a fourth signal representative of light collected by the fourth pixel, the fourth signal representative of a combination of the third color component and the fluorescence illumination.

7. The system of claim 6, wherein the image processing system is further configured to:
subtract the second signal from the third signal to identify a fluorescence illumination component of the third signal that is representative of the fluorescence illumination;
subtract the fluorescence illumination component from the first signal to generate a processed first signal representative of only the first color component; and
subtract the fluorescence illumination component from the fourth signal to generate a processed fourth signal representative of only the third color component.

8. The system of claim 7, wherein the image processing system is further configured to:
receive a command to present a full-color image that does not include a fluorescence image, and
in response to the command, generate the full-color image based on the processed first signal, the second signal, and the processed fourth signal.

9. The system of claim 8, wherein the image processing system is further configured to:
receive a command to present a full-color fluorescence image, and
in response to the command, generate the full-color fluorescence image based on the processed first signal, the second signal, the processed fourth signal, and the fluorescence illumination component.

10. The system of claim 1, further comprising:
a first color filter that covers the first pixel and that is configured to allow the first pixel to collect a first color component of visible light and prevent the first pixel from collecting second and third color components of the visible light;
a second color filter that covers the second and third pixels, the second color filter configured to allow the second and third pixels to each collect the second color component of the visible light and prevent the second and third pixels from each collecting the first and third color components of the visible light; and
a third color filter that covers the fourth pixel and that is configured to allow the fourth pixel to collect the third color component of the visible light and prevent the fourth pixel from collecting the first and second color components of the visible light.

11. The system of claim 10, wherein:
the first color filter comprises a red filter configured to prevent the first pixel from collecting blue and green components of the visible light;
the second color filter comprises a blue filter configured to prevent the second and third pixels from each collecting the red and green components of the visible light; and
the third color filter comprises a green filter configured to prevent the fourth pixel from collecting the red and blue components of the visible light.

12. The system of claim 10, wherein:
the first color filter comprises a red filter configured to prevent the first pixel from collecting blue and green components of the visible light;
the second color filter comprises a green filter configured to prevent the second and third pixels from each collecting the blue and red components of the visible light; and
the third color filter comprises a blue filter configured to prevent the fourth pixel from collecting the green and red components of the visible light.

13. The system of claim 1, wherein the pixel-level broadband infrared cutoff filter comprises a coating configured to adhere to a surface of the second pixel.

14. The system of claim 1, wherein the first, second, third, and fourth pixels are arranged in a two-by-two array of pixels.

* * * * *